United States Patent
Cho et al.

(10) Patent No.: US 10,548,517 B2
(45) Date of Patent: Feb. 4, 2020

(54) SPECTROSCOPIC APPARATUS FOR BIOLOGICAL MATERIAL AND SPECTROSCOPIC METHOD USING THE SAME

(71) Applicants: SAMSUNG ELECTRONICS CO., LTD., Suwon-si (KR); IMEC VZW, Leuven (BE)

(72) Inventors: Seongho Cho, Gwacheon-si (KR); Peter Peumans, Herne (BE); Woochang Lee, Anyang-si (KR)

(73) Assignees: SAMSUNG ELECTRONICS CO., LTD., Suwon-si (KR); IMEC VZW, Leuven (BE)

( * ) Notice: Subject to any disclaimer, the term of this patent is extended or adjusted under 35 U.S.C. 154(b) by 1125 days.

(21) Appl. No.: 14/934,727

(22) Filed: Nov. 6, 2015

(65) Prior Publication Data

US 2016/0128612 A1    May 12, 2016

(30) Foreign Application Priority Data

Nov. 7, 2014  (KR) ............ 10-2014-0154734

(51) Int. Cl.
*A61B 5/1455* (2006.01)
*A61B 5/145* (2006.01)

(52) U.S. Cl.
CPC ........ *A61B 5/1455* (2013.01); *A61B 5/14532* (2013.01); *G01N 2201/12* (2013.01)

(58) Field of Classification Search
CPC . A61B 5/1455; A61B 5/0075; A61B 5/14532; A61B 2562/043; A61B 5/14551; A61B 5/7271; G01N 2201/12
See application file for complete search history.

(56) References Cited

U.S. PATENT DOCUMENTS 6,681,133 B2 *  1/2004  Chaiken ............... A61B 5/0059
                                                          372/29.02
7,362,426 B1    4/2008  Yoo
(Continued)

FOREIGN PATENT DOCUMENTS

JP    2013-113620 A    6/2013
JP    2014-066677 A    4/2014
(Continued)

OTHER PUBLICATIONS

Matousek et al., "Numerical Simulations of Subsurface Probing in Diffusely Scattering Media Using Spatially Offset Raman Spectroscopy", Applied Spectroscopy, vol. 59(12), Sep. 2005, pp. 1485-1492 (Year: 2005).*
Matousek et al., Subsurface Probing in Diffuse Scattered Media Using Spatially Offset Raman Spectroscopy, Applied Spectroscopy, vol. 59(4), Jan. 2005, pp. 393-400 (Year: 2005).*
(Continued)

*Primary Examiner* — Eric F Winakur
*Assistant Examiner* — Chu Chuan Liu
(74) *Attorney, Agent, or Firm* — Sughrue Mion, PLLC

(57) ABSTRACT

A spectroscopic apparatus and method for analyzing a biological material are provided. The spectroscopic apparatus may analyze a biological material which has an internal non-uniform tissue depending on a position thereof. The apparatus may include at least one detector configured to obtain respective detection spectrums corresponding to a plurality of measurement regions that are at mutually different positions of the biological material, and an information processor to determine whether the measurement regions are normal by mutually comparing the detection spectrums, or converting contribution degrees of data for a specific component of the biological material by differentiating the detection spectrums.

23 Claims, 4 Drawing Sheets

(56) References Cited

U.S. PATENT DOCUMENTS

| | | | | |
|---|---|---|---|---|
| 2005/0010130 A1* | 1/2005 | Morris | ................. | A61B 5/0059 600/562 |
| 2008/0076985 A1* | 3/2008 | Matousek | ............. | A61B 5/0059 600/310 |
| 2008/0117416 A1* | 5/2008 | Hunter | ................. | A61B 5/0066 356/301 |
| 2014/0052386 A1 | 2/2014 | Guenther et al. | | |

FOREIGN PATENT DOCUMENTS

| | | |
|---|---|---|
| JP | 5460528 B2 | 4/2014 |
| JP | 2014-098653 A | 5/2014 |
| KR | 10-1350402 B1 | 1/2014 |

OTHER PUBLICATIONS

Yudovsky, et al.; "Rapid and Accurate Estimation of Blood Saturation, Melanin Content, and Epidermis Thickness from Spectral Diffuse Reflectance", Applied Optics, Apr. 2010, vol. 49, No. 10, 13 pages total.

Lipson, Jan, et al. "Requirements for calibration in noninvasive glucose monitoring by Raman spectroscopy." Journal of diabetes science and technology 3.2 (2009): 233-241.†

Barman, Ishan, et al. "Accurate spectroscopic calibration for non-invasive glucose monitoring by modeling the physiological glucose dynamics." Analytical chemistry 82.14 (2010): 6104-6114.†

Enejder, Annika MK, et al. "Raman spectroscopy for noninvasive glucose measurements." Journal of biomedical optics 10.3 (2005): 031114-0311149.†

\* cited by examiner
† cited by third party

SPECTROSCOPIC APPARATUS FOR BIOLOGICAL MATERIAL AND SPECTROSCOPIC METHOD USING THE SAME

CROSS-REFERENCE TO RELATED APPLICATION

This application claims priority from Korean Patent Application No. 10-2014-0154734, filed on Nov. 7, 2014 in the Korean Intellectual Property Office, the disclosure of which is incorporated herein in its entirety by reference.

BACKGROUND

1. Field

Apparatuses and methods consistent with exemplary embodiments relate to a spectroscopic apparatus for analyzing a biological material and a spectroscopic method using the same.

2. Description of Related Art

Spectroscopy is a technology for analyzing a biological material such as a piece of skin. For example, spectroscopy may use fixed focus and fixed measurement regions to reduce measurement error and to secure reproducibility. However, if a foreign substance is included on the skin such as a strand of hair or sweat from a sweat gland measurement of the skin can be difficult because a measurement error may occur. Accordingly, the skin may be measured again for better results after changing the position of the measurement region to compensate for the inclusion of the foreign substance.

Recently, progress has been made in the development of a technique which extends an application range of a Near Infrared Spectrometer (NIRS) or a Raman spectrometer by microminiaturization, which can provide a user with a simplified measurement thereof. For example, a measurement technique for a biological material such as a piece of skin which uses the microminiaturized spectrometer may significantly improve a range or a frequency of the measurement.

SUMMARY

Provided are a spectroscopic apparatus for analyzing a biological material and a spectroscopic method using the same.

Additional aspects will be set forth in part in the description which follows and, in part, will be apparent from the description, or may be learned by practice of one or more of the exemplary embodiments.

According to an aspect of an exemplary embodiment, provided is a spectroscopic apparatus for analyzing a biological material that has an internal non-uniform tissue depending on a position thereof, the apparatus including at least one detector configured to obtain respective detection spectrums corresponding to a plurality of measurement regions that are at mutually different positions of the biological material; and an information processor configured to compare or differentiate the detection spectrums.

Each of the measurement regions may have a multi-layered structure including two or more stacked layers, and the two or more layers may have a non-uniform thickness depending on position of each of the measurement regions.

Furthermore, the two or more layers forming each of the measurement regions may differ from one another in contribution degrees for the detection spectrum of each of the measurement regions.

The information processor may determine whether the measurement regions are normal by mutually comparing the respective detection spectrums. Also, the information processor may convert differential spectrums that are obtained by differentiating the detection spectrums into contribution degrees of data for a target analyte of the biological material. In addition, the information processor may calculate a target measurement value for the target analyte of the biological material at an optional time using the converted contribution degrees of data for the target analyte of the biological material.

The at least one detector may obtain the detection spectrums using a Raman spectroscopy or a near infrared spectroscopy. Each detector may be adjacent to a surface of the biological material and may include an aperture through which a light signal from the measurement region is received.

The biological material may be a piece of skin, and the spectroscopic apparatus may measure blood glucose in real time using the detection spectrums that may be obtained at different positions on the skin.

According to an aspect of another exemplary embodiment, provided is a spectroscopic method for analyzing a biological material that has an internal non-uniform tissue depending on a position thereof, the method including obtaining respective detection spectrums corresponding to a plurality of measurement regions that are at mutually different positions of the biological material; and determining whether the measurement regions are normal by mutually comparing the respective detection spectrums.

Each of the measurement regions may have a multi-layered structure including two or more stacked layers, and each of the two or more layers may have a non-uniform thickness depending on positions of the measurement regions. Furthermore, the spectroscopic method may further include changing a position of a measurement region that is determined as an abnormal measurement region, from among the plurality of measurement regions.

According to an aspect of another exemplary embodiment, provided is a spectroscopic method for analyzing a biological material that has an internal non-uniform tissue depending on a position thereof, the method including obtaining respective detection spectrums corresponding to a plurality of measurement regions that are at mutually different positions of the biological material; differentiating the detection spectrums; and converting the differentiated detection spectrums into contribution degrees of data for a target analyte of the biological material.

Each of the measurement regions may have a multi-layered structure that includes two or more stacked layers, and the two or more layers may have a non-uniform thickness depending on the position of each of the measurement regions. Furthermore, the two or more layers forming each of the measurement regions may differ from one another in contribution degrees for the detection spectrum of each of the measurement regions.

The spectroscopic method may further include calculating a target measurement value for the target analyte of the biological material at an optional time using the converted contribution degree of data for a specific component of the biological material.

The calculating a target measurement value for the target analyte may further include measuring actual values for the target analyte of the biological material at a first point in time; converting differential spectrums that are obtained by differentiating the detection spectrums that are acquired at the first point in time into first contribution degrees of data for the target analyte of the biological material; correlating the first contribution degrees of data to the actual measured values that are measured at the first point in time; converting differential spectrums that are obtained by differentiating the detection spectrums that are acquired at a second point in time into second contribution degrees of data for the target analyte of the biological material; and calculating the target measurement value for the target analyte of the biological material at the second point in time by comparing the second contribution degrees of data with the first contribution degrees of data.

BRIEF DESCRIPTION OF THE DRAWINGS

These and/or other aspects will become apparent and more readily appreciated from the following description of exemplary embodiments with reference to the accompanying drawings, in which.

DETAILED DESCRIPTION

Figure 1:
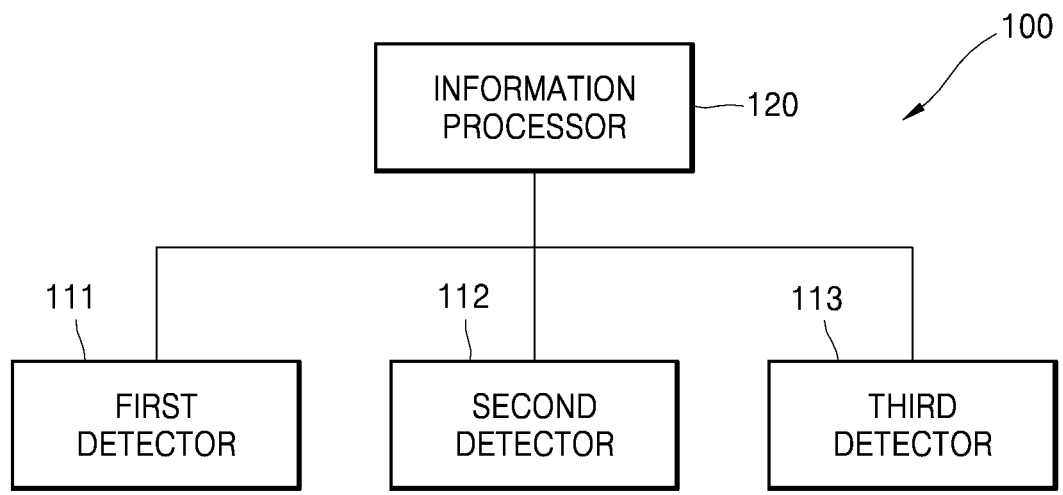
FIG. 1 is a block diagram of a spectroscopic apparatus for a biological material according to an exemplary embodiment.

Reference will now be made in detail to the exemplary embodiments, examples of which are illustrated in the accompanying drawings, wherein like reference numerals should be understood to refer to like elements throughout. In this regard, one or more of the exemplary embodiments may have different forms and should not be construed as being limited to the descriptions set forth herein. Accordingly, the exemplary embodiments are merely described below, by referring to the figures, to explain exemplary aspects.

Also, it should be understood that when a component, such as a layer, a film, a region, a plate, and the like, is referred to as being "on" another component, the component may be directly on the other component or one or more intervening components may be present thereon. As used herein, the term "and/or" includes any and all combinations of one or more of the associated listed items. Also, expressions such as "at least one of," when preceding a list of elements, should be understood to modify the entire list of elements and not to modify the individual elements of the list.

FIG. 1 is a schematic block diagram of a spectroscopic apparatus for a biological material according to an exemplary embodiment.

Figure 2:
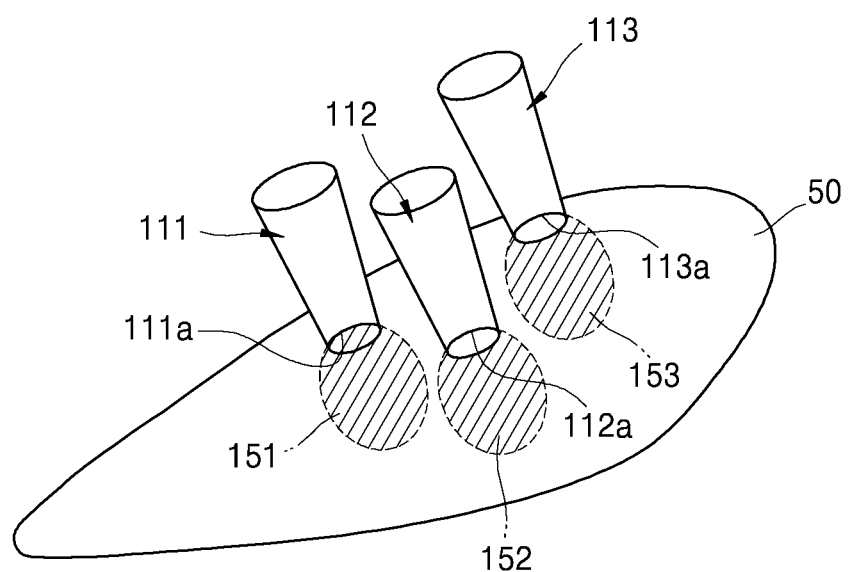
FIG. 2 is a diagram illustrating detectors of the spectroscopic apparatus of FIG. 1 which are provided on measurement regions of a biological material, according to an exemplary embodiment.

Referring to FIG. 1, the spectroscopic apparatus 100 may be used to detect and/or analyze a target analyte in a specimen. A biological material 50 (as shown in FIG. 2) which has an internal non-uniform tissue depending on a position thereof, may be used as the specimen in this example. For example, the biological material 50 may be a piece of skin from a human body in which the structure, thickness, and/or components of inner layers of the skin may change depending on a position thereof. In this example, the spectroscopic apparatus 100 may detect a blood glucose level using spectral spectrums measured at mutually different positions on the skin, in real-time. For example, in real-time may be a detection which occurs without delay, but is not limited thereto. Also, the spectroscopic apparatus 100 may be used to detect various target analytes in the biological material in addition to or other than detecting a blood glucose level.

In the example of FIG. 1, the spectroscopic apparatus 100 includes a plurality of detectors 111, 112, and 113, and an information processor 120. A plurality of measurement regions 151, 152, and 153 (shown in FIG. 2) are provided on the mutually different positions of the biological material 50, and the plurality of detectors 111, 112, and 113 measure respective detection spectrums corresponding to the measurement regions 151, 152, and 153. As an example, each of the measurement regions 151, 152, and 153 may be a three-dimensional (3D) region with a specified shape that is formed from a surface of the biological material 50 to a specified depth thereof.

The detectors 111, 112, and 113 may measure the detection spectrums corresponding to the measurement regions 151, 152, and 153 on the biological material 50 using a normal, noninvasive, and nondestructive spectroscopy. For example, the detectors 111, 112, and 113 may use a Raman spectroscopy, a near infrared spectroscopy, and the like. The detectors 111, 112, and 113 may measure the detection spectrums simultaneously or sequentially at a specified time interval.

FIG. 1 illustrates an example in which the spectroscopic apparatus 100 includes first to third detectors 111, 112, and 113 as an example. As another example, the spectroscopic apparatus 100 may include various numbers of detectors. For example, the spectroscopic apparatus 100 may include one or more detection units. In an example in which the spectroscopic apparatus 100 includes one detector, the detector may measure the detection spectrums corresponding to the measurement regions 151, 152, and 153 while moving.

The information processor 120 compares or differentiates the detection spectrums that are obtained from the detectors 111, 112, and 113. For example, the information processor 120 may determine whether the measurement regions 151, 152, and 153 are normal by mutually comparing the detection spectrums that are obtained from the detectors 111, 112, and 113. Furthermore, the information processor 120 may differentiate the detection spectrums obtained from the detectors 111, 112, and 113, and may convert the differentiated spectrum into contribution degrees of data for a target analyte of the biological material 50. In addition, the information processor 120 may calculate a target measurement value for the target analyte of the biological material at an optional time using the converted contribution degrees of data for the target analyte of the biological material 50.

FIG. 2 is a diagram illustrating the detectors 111, 112, and 113 of the spectroscopic apparatus that are provided on the measurement regions 151, 152, and 153 of the biological material 50 according to an exemplary embodiment. According to one or more exemplary embodiments, the measurement regions 151, 152, and 153 may be provided on three mutually different positions of the biological material 50 as described in the example below, but the exemplary embodiments are not limited thereto. As another example, two, four, or more than four measurement regions may be provided on the mutually different positions of the biological material 50.

Referring to FIG. 2, the first to third detectors 111, 112, and 113 are provided adjacent to a surface of the biological material 50. In this example, first to third apertures 111a, 112a, and 113a through which a light signal from the biological material 50 may pass are provided in the first to third detection units 111, 112, and 113, and are adjacent to the first to third measurement regions 151, 152, and 153 of the biological material 50. For example, light emitted from a light source (not shown) provided in the first detector 111 enters the surface of the biological material 50 through the first aperture 111a. Accordingly, a light signal from the first measurement region 151 may be formed from the surface of the biological material 50 to a specified depth thereof, and may be accommodated or received in the first detector 111 through the first aperture 111a. In addition, the first detector 111 may measure a first detection spectrum corresponding to the first measurement region 151 on the biological material 50 using the light signal accommodated in the first detector 111 through the first aperture 111a. Likewise, the second detector 112 may measure a second detection spectrum corresponding to the second measurement region 152 of the biological material 50 using a light signal accommodated in the second detector 112 through the second aperture 112a. In addition, the third detector 113 may measure a third detection spectrum corresponding to the third measurement region 153 of the biological material 50 using a light signal accommodated in the third detector 113 through the third aperture 113a.

As a non-limiting example, the width of the measurement regions 151, 152, and 153 may be controlled by and may be bigger than, equal to, or smaller than a width of the respective apertures 111a, 112a, and 113a, of the first through third detectors 111, 112, and 113. In this example, a width of a measurement region (151, 152, or 153) becomes larger as the respective region extends from the aperture towards a center of the region, and tapers off further down in biological material 50 until the end of the region generating an approximate shape of a three-dimensional (3D) ellipse.

An example of a method of determining whether the measurement regions 151, 152, and 153 provided on the mutually different positions of the biological material 50 are normal, or detecting a target analyte of the biological material 50 that is to be analyzed, using the spectroscopic apparatus 100, is described below.

Figure 3:
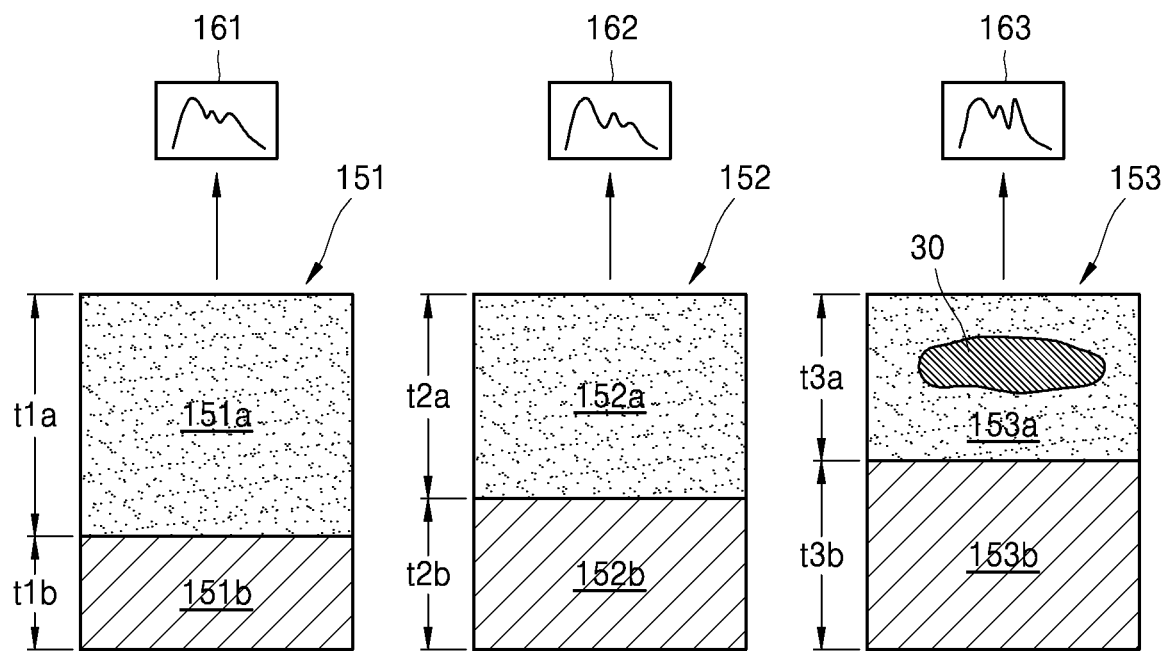
FIG. 3 is a diagram illustrating cross-sections of the measurement regions illustrated in FIG. 2.

FIG. 3 is a diagram illustrating cross-sections of the measurement regions illustrated in FIG. 2.

Referring to FIG. 3, each of the measurement regions 151, 152, and 153 may have a multi-layered structure in which two or more layers are vertically laminated or stacked such that at least one layer is overlaid on another layer. That is, in this example, the measurement regions are divided into multiple layers. FIG. 3 illustrates a structure in which a first upper layer 151a and a first lower layer 151b are laminated in the first measurement region 151, a structure in which a second upper layer 152a and a second lower layer 152b are laminated in the second measurement region 152, and a structure in which a third upper layer 153a and a third lower layer 153b are laminated in the third measurement region 153. The upper layers 151a, 152a, and 153a and the lower layers 151b, 152b, and 153b may include mutually different materials. As another example, unlike FIG. 3, each of the first to third measurement regions 151, 152, and 153 may have a structure in which three or more layers are laminated.

Furthermore, the first to third upper layers 151a, 152a, and 153a may have different thicknesses t1a, t2a, and t3a, respectively, and the first to third lower layers 151b, 152b, and 153b may also have different thicknesses t1b, t2b, and t3b, respectively. In this example, the first upper layer 151a has the largest thickness t1a and the third upper layer 153a has the smallest thickness t3a, from among the first to third upper layers 151a, 152a, and 153a. In addition, the third lower layer 153b has the largest thickness t3b and the first lower layer 151b has the smallest thickness t1b, from among the first to third lower layers 151b, 152b, and 153b. As also shown in FIG. 3, a foreign substance 30, which is not included in the first and second measurement regions 151 and 152, is included in the third upper layer 153a of the third measurement region 153.

Figure 4:
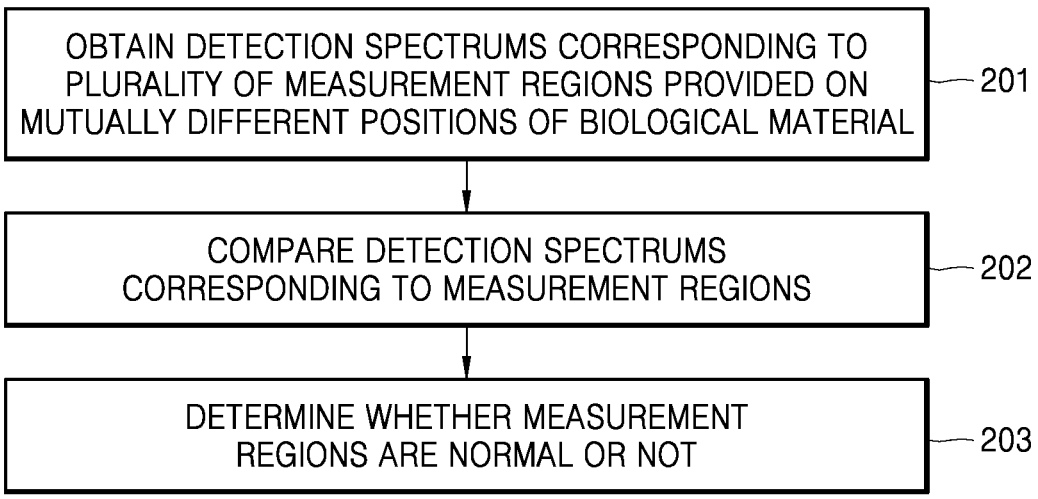
FIG. 4 is a flowchart of a method of analyzing detection spectrums corresponding to the measurement regions illustrated in FIG. 3 and determining whether the measurement regions are normal, according to an exemplary embodiment.

FIG. 4 is a flowchart of a method of analyzing the detection spectrums corresponding to the measurement regions illustrated in FIG. 3 and determining whether the measurement regions are normal, according to an exemplary embodiment.

Referring to FIG. 4, the detectors 111, 112, and 113 (of FIG. 1) measure the detection spectrums 161, 162, and 163 corresponding to the measurement regions 151, 152, and 153 provided on or at the mutually different positions of the biological material 50 (of FIG. 2) (operation 201). For example, the first to third detectors 111, 112, and 113 may measure the first to third detection spectrums 161, 162, and 163 corresponding to the first to third measurement regions 151, 152, and 153. Here, the first to third detectors 111, 112, and 113 may measure the first to third detection spectrums 161, 162, and 163 using, for example, a noninvasive and nondestructive spectroscopy such as a Raman spectroscopy, a near infrared spectroscopy, and the like. As another example, one detector or a single detector (not shown) may measure the first to third detection spectrums 161, 162, and 163 while the detector moves along the first to third measurement regions 151, 152, and 153.

Because the upper layers 151a, 152a, and 153a and the lower layers 151b, 152b, and 153b of the measurement regions 151, 152, and 153 may have mutually different materials and/or mutually different thicknesses, the upper layers 151a, 152a, and 153a and the lower layers 151b, 152b, and 153b may differ from one another in contribution degrees for the detection spectrums 161, 162, and 163 of the measurement regions 151, 152, and 153. For example, the contribution degrees of the upper layers 151a, 152a, and 153a for the detection spectrums 161, 162, and 163, may be higher than the contribution degrees of the lower layers 151b, 152b, and 153b. However, the exemplary embodiments are not limited thereto, and contribution degrees of the lower layers 151b, 152b, and 153b for the detection spectrums 161, 162, and 163, may be higher than the contribution degrees of the upper layers 151a, 152a, and 153a.

Next, the information processor 120 compares the detection spectrums 161, 162, and 163 corresponding to the measurement regions 151, 152, and 153 of the biological material 50 (operation 202), and determines whether the measurement regions 151, 152, and 153 are normal (operation 203). For example, the information processor 120 may compare the first to third detection spectrums 161, 162, and 163 corresponding to the first to third measurement regions 151, 152, and 153, and then determine whether there is a detection spectrum that includes a noise signal or an abnormal signal from among the first to third detection spectrums 161, 162, and 163.

For example, in FIG. 3 the foreign substance 30 is included in the upper layer 153a of the third measurement region 153. In this example, the third detection spectrum 163 may have a shape that differs from the shapes of the first and second detection spectrums 161 and 162 due to the generation of a noise signal by the foreign substance 30. Accordingly, because the third measurement region 153 includes the foreign substance 30 that generates the noise signal, a determination can be made that the third measurement region 153 is provided on or at an abnormal position which may obstruct analysis of the target analyte of the biological material 50. In this example, because the third measurement region 153 is provided on an abnormal position which may obstruct analysis of the target analyte of the biological material 50, the third measurement region 153 may be shifted to a normal position which is proper or otherwise better for analyzing of the target analyte by moving the third detector 113.

As described above, the abnormal position may obstruct analysis of a target analyte of the biological material 50 and may be avoided by mutually comparing the detection spectrums 161, 162, and 163 corresponding to the measurement regions 151, 152, and 153, and sensing a noise signal or an abnormal signal which may occur due to a position of each of the measurement regions 151, 152, and 153. Therefore, only a spectrum signal that has a high contribution degree corresponding to the target analyte of the biological material 50 may be selected, and a signal to noise (SNR) may be improved or otherwise reduced or controlled. For example, only a spectrum signal that has a contribution degree corresponding to the target analyte that is equal to or greater than a threshold value may be selected.

Figure 5:
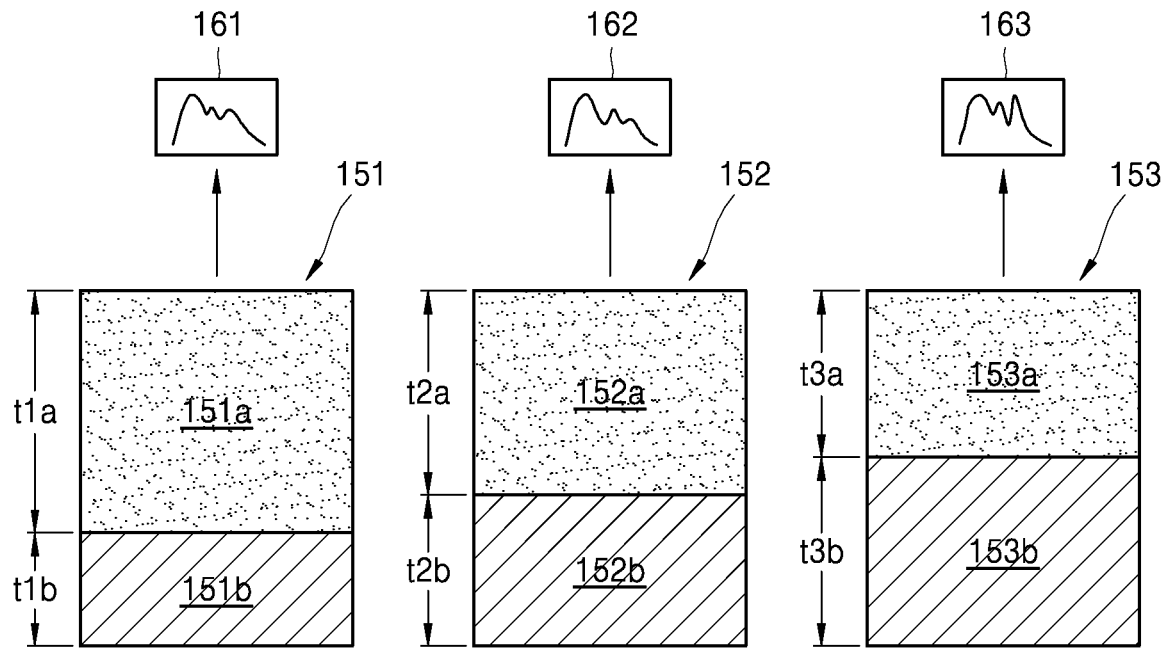
FIG. 5 is another diagram illustrating the cross-sections of the measurement regions illustrated in FIG. 2.

FIG. 5 is a diagram illustrating cross-sections of the measurement regions illustrated in FIG. 2 according to another exemplary embodiment.

Referring to FIG. 5, each of the measurement regions 151, 152, and 153 includes a multi-layered structure in which two or more layers are vertically laminated such that at least one layer is overlaid on another layer. FIG. 5 shows a structure in which the first upper layer 151a and the first lower layer 151b are laminated in the first measurement region 151, a structure in which the second upper layer 152a and the second lower layer 152b are laminated in the second measurement region 152, and a structure in which the third upper layer 153a and the third lower layer 153b are laminated in the third measurement region 153. The upper layers 151a, 152a, and 153a and the lower layers 151b, 152b, and 153b may include mutually different materials. As another example, unlike as shown in FIG. 5, each of the first to third measurement regions 151, 152, and 153 may have a structure in which three or more layers are laminated.

Furthermore, the first to third upper layers 151a, 152a, and 153a may have different thicknesses t1a, t2a, and t3a, and the first to third lower layers 151b, 152b, and 153b may also have different respective thicknesses t1b, t2b, and t3b. In the example of FIG. 5, the first upper layer 151a has the largest thickness t1a and the third upper layer 153a has the smallest thickness t3a, from among the first to third upper layers 151a, 152a, and 153a. In addition, the third lower layer 153b has the largest thickness t3b and the first lower layer 151b has the smallest thickness t1b, from among the first to third lower layers 151b, 152b, and 153b. Because the upper layers 151a, 152a, and 153a and the lower layers 151b, 152b, and 153b may have mutually different materials and mutually different thicknesses, the upper layers 151a, 152a, and 153a and the lower layers 151b, 152b, and 153b may differ from one another in an amount of contribution degrees for the detection spectrums 161, 162, and 163 of the measurement regions 151, 152, and 153.

Figure 6:
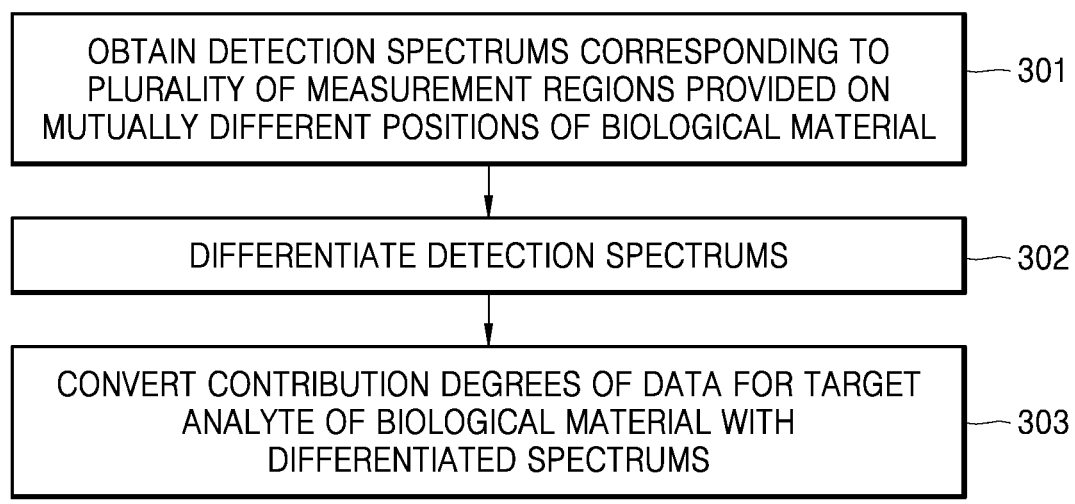
FIG. 6 is a flowchart of a method of analyzing detection spectrums corresponding to the measurement regions illustrated in FIG. 5 and detecting a target analyte of a biological material, according to an exemplary embodiment.

FIG. 6 is a flowchart of a method of analyzing the detection spectrums corresponding to the measurement regions illustrated in FIG. 5 and detecting a target analyte of a biological material, according to an exemplary embodiment.

Referring to FIG. 6, the detectors 111, 112, and 113 (of FIG. 1) measure the detection spectrums 161, 162, and 163 corresponding to the measurement regions 151, 152, and 153 which are provided on the mutually different positions of the biological material 50 (of FIG. 2) (operation 301). For example, the first to third detectors 111, 112, and 113 may measure the detection spectrums 161, 162, and 163 corresponding to the measurement regions 151, 152, and 153. The first to third detectors 111, 112, and 113 may measure the first to third detection spectrums 161, 162, and 163 using, for example, a noninvasive and nondestructive spectroscopy such as Raman spectroscopy, near infrared spectroscopy, and the like. Alternatively, one detector (not shown) may measure the first to third detection spectrums 161, 162, and 163 while moving along the first to third measurement regions 151, 152, and 153.

As described above, because the upper layers 151a, 152a, and 153a and the lower layers 151b, 152b, and 153b in the measurement regions 151, 152, and 153 may include mutually different materials and/or mutually different thicknesses, the upper layers 151a, 152a, and 153a and the lower layers 151b, 152b, and 153b may differ from one another in degrees of contribution for the detection spectrums 161, 162, and 163 of the measurement regions 151, 152, and 153. For example, the contribution degrees of the upper layers 151a, 152a, and 153a for the detection spectrums 161, 162, and 163 of the measurement regions 151, 152, and 153, are higher than those of the lower layers 151b, 152b, and 153b. In this example, a target analyte of the biological material 50 to be analyzed may exist in the lower layers 151b, 152b, and 153b. However, the exemplary embodiments are not limited thereto, and in some examples the contribution degrees of the lower layers 151b, 152b, and 153b for the detection spectrums 161, 162, and 163 of the measurement regions 151, 152, and 153, may be equal to or higher than those of the upper layers 151a, 152a, and 153a.

Next, the detection spectrums 161, 162, and 163 corresponding to the measurement regions 151, 152, and 153 on the biological material 50 are differentiated, for example, using the information processor 120 (operation 302), and the differentiated spectrums are converted into contribution degrees of data for the target analyte of the biological material 50 (operation 303). Furthermore, a target measurement value for the target analyte included in the biological material 50 may be calculated at an optional time using the converted contribution degrees of data.

An example of a detection method of the target analyte of the biological material 50 that may be performed by analyzing the first and second measurement regions 151 and 152 corresponding to the first and second detection spectrums 161 and 162 from among the measurement regions 151, 152, and 153 of FIG. 5 is described below. In this example, the contribution degrees of the upper layers 151a and 152a for the detection spectrums 161 and 162 of the first and second measurement regions 151 and 152, are significantly higher than those of the lower layers 151b and 152b. As a non-limiting example, the contribution degrees of the upper layer 151a and the lower layer 151b corresponding to the first detection spectrum 161 in the first measurement region 151 may be 99% and 1%, respectively, and the contribution degrees of the upper layer 152a and the lower layer 152b corresponding to the second detection spectrum 162 in the second measurement region 152 may be 98% and 2%, respectively. In this case, the target analyte of the biological material 50 to be analyzed may exist in the lower layers 151b and 152b of the first and second measurement regions 151 and 152.

Actual measured values for the target analyte of the biological material 50 to be analyzed may be determined at a first point in time. The actual measured values may be determined by extracting the target analyte in the biological material 50 at the first point in time. Next, the first and second detection spectrums 161 and 162 corresponding to the first and second measurement regions 151 and 152 may be measured at the first point in time, and the first and second detection spectrums 161 and 162 may be differentiated from each other.

In this example, pieces of data of the first and second upper layers 151a and 152a having the high contribution degrees corresponding to the first and second detection spectrums 161 and 162 may be interpreted as being mutually canceled. For example, if the contribution degrees of the first upper layer 151a and the first lower layer 151b corresponding to the first detection spectrum 161 in the first measurement region 151 are 99% and 1%, respectively, and the contribution degrees of the second upper layer 152a and the second lower layer 152b corresponding to the second detection spectrum 162 in the second measurement region 152 are 98% and 2%, respectively, the contribution degree of the first upper layer 151a is almost the same as that of the second upper layer 152a. In this example, the contribution degrees of the first and second upper layers 151a and 152a are so low that they may be ignored as compared with those of the lower layers 151b and 152b, in differential spectrums that are obtained by differentiating the first and second detection spectrums 161 and 162.

Accordingly, the differential spectrums obtained by differentiating the first and second detection spectrums 161 and 162 at the first point in time may be considered to include only the data of a target analyte resulting from a thickness difference between the first and second lower layers 151b and 152b. Next, the differential spectrums that are obtained at the first point in time may be converted into first contribution degrees of data for the actual measured values of the target analyte. Thus, the first contribution degrees of data may correspond to the actual measured values determined at the first point in time.

Next, the first and second detection spectrums 161 and 162 corresponding to the first and second measurement regions 151 and 152 may be measured at a second point in time, and the first and second detection spectrums 161 and 162 may be mutually differentiated. For example, the differential spectrums obtained by differentiating the first and second detection spectrums 161 and 162 at the second point in time may include only the data of the target analyte resulting from the thickness difference between the first and second detection spectrums 161 and 162. Next, the differential spectrums obtained at the second point in time may be converted into second contribution degrees of data.

As described above, because the first contribution degrees of data converted at the first point in time may correspond to the actual measured values with respect to the target analyte at the first point in time, a target measurement value to be measured for the target analyte at the second point in time may be calculated by comparing the second contribution degrees of data converted at the second point in time with the first contribution degrees of data. In the above non-limiting example, only the two measurement regions 151 and 152 are used for calculating the first and second contribution degrees of data. As another example, a more accurate target measurement value for the target analyte to be analyzed may be obtained by increasing the number of the measurement regions that are provided on the mutually different positions.

As described above, the detection spectrums corresponding to the measurement regions that are provided on the mutually different positions of the biological material 50 may be measured, and the detection spectrums may be differentiated. Thus, the target measurement value to be measured corresponding to the target analyte of the biological material may be calculated in real time.

Figure 7:
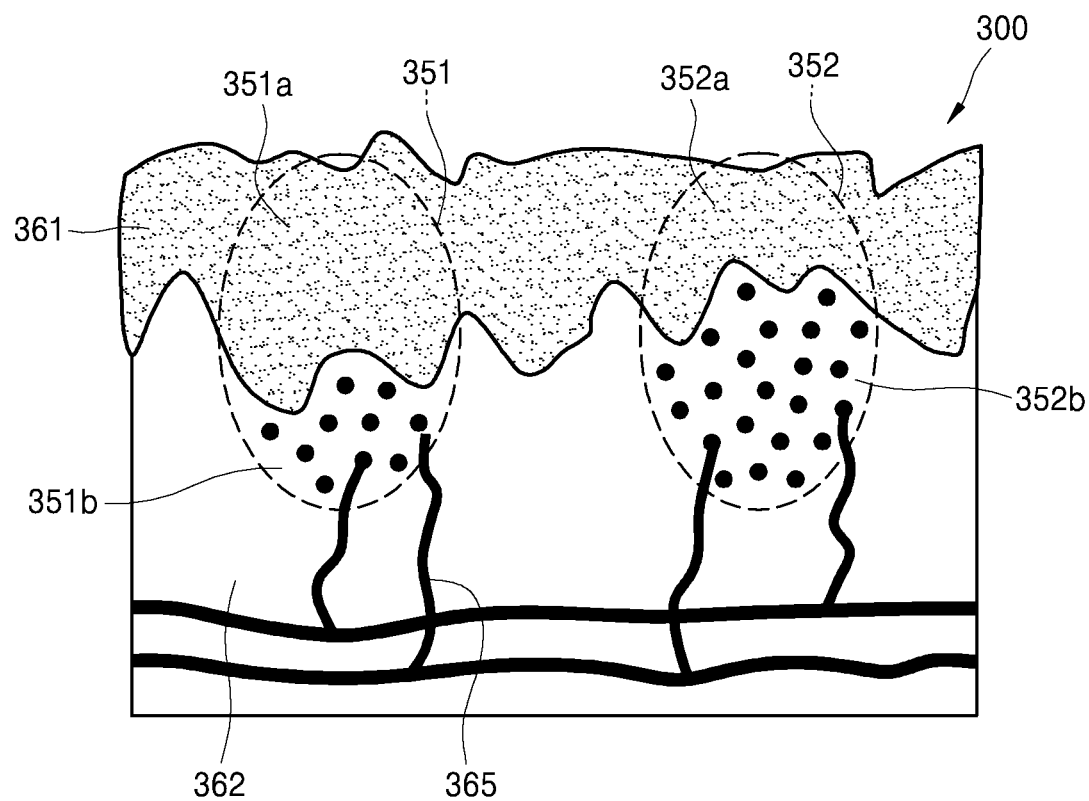
FIG. 7 is a diagram illustrating a cross sectional structure of a piece of skin.

FIG. 7 is a diagram of a cross sectional structure of a piece of skin according to an exemplary embodiment. Referring to FIG. 7, a piece of skin 300 has a layered structure that includes an epidermal layer 361 disposed above a dermal layer 362. Here, blood flows in capillary tubes 365 in the dermal layer 362. In this example, each of the epidermal layer 361 and the dermal layer 362 has a non-uniform thickness depending on a position thereof. Here, a blood glucose level may be calculated. An example of a blood glucose level calculating method at an optional time by analyzing the skin 300 of FIG. 7 by the spectroscopic method for the biological material is described below. For example, the blood glucose level may be measured by the information processor 120 illustrated in the example of FIG. 1.

Figure 8:
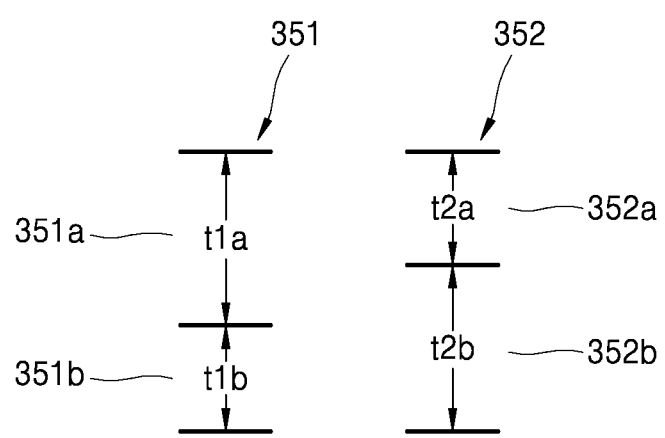
FIG. 8 is a diagram illustrating an average thickness of an epidermal layer and a dermal layer of the piece of skin illustrated in FIG. 7.

First, an actual blood glucose level at the first point in time may be measured by extracting blood in the skin 300 at the first point in time. Next, the first and second measurement regions 351 and 352 may be set at mutually different positions of the skin. FIG. 8 is a diagram illustrating an average thickness of each of the epidermal layers 351a and 352a and the dermal layers 351b and 352b in the first and second measurement regions 351 and 352. FIG. 8 shows an example in which the average thickness t1a of the first epidermal layer 351a in the first measurement region 351 is larger than the average thickness t2a of the second epidermal layer 352a in the second measurement region 352, and the average thickness t1b of the first dermal layer 351b in the first measurement region 351 is larger than the average thickness t2b of the second dermal layer 352b in the second measurement region 352.

In this example, first and second detection spectrums corresponding to the first and second measurement regions 351 and 352 may be measured at a first point in time. Generally, the contribution degrees of the first and second epidermal layers 351a and 352a corresponding to the first and second detection spectrums, may be much higher than those of the dermal layers 351b and 352b.

Next, the differential spectrums may be calculated by differentiating the first and second detection spectrums. When the first and second detection spectrums are mutually differentiated, data of the first and second epidermal layer 351a and 352a that have high contribution degrees corresponding to the first and second detection spectrums may be interpreted as being mutually canceled. Thus, the differential spectrums that are obtained by differentiating the first and second detection spectrums at the first point in time may include only the data for blood glucose resulting from a thickness difference between the first and second dermal layer 351b and 352b. In addition, the differential spectrums obtained at the first point in time may be converted into first contribution degrees of data for the actual blood glucose level. For example, the first contribution degrees of data may correspond to the actual blood glucose level measured at the first point in time.

Next, the first and second detection spectrums corresponding to the first and second measurement regions 351 and 352 may be measured at the second point in time, and the first and second detection spectrums are mutually differentiated. In this example, the differential spectrums obtained at the second point in time may be converted into second contribution degrees of data. Because the first contribution degrees of data correspond to the actual blood glucose level at the first point in time, a target blood glucose level to be calculated at the second point in time may be calculated by comparing the second contribution degrees of data converted at the second point in time with the first contribution degree of data. Alternatively, although only the two measurement regions 351 and 352 are used in the above, a more accurate blood glucose level may be obtained by increasing the number of the measurement regions.

According to one or more exemplary embodiments, provided is a spectroscopic apparatus and method for detecting a biological material. The apparatus may include a detector configured to obtain a plurality of detection spectrums from a plurality of measurement regions, respectively, of the biological material. The apparatus may also include an information processor configured to compare the plurality of detection spectrums with each other to detect at least one detection spectrum that includes noise, and calculate a target measurement value for an analyte of the biological material using the detection spectrums which do not include the noise.

As described above, according to one or more exemplary embodiments, an abnormal position which may obstruct measurement of a target analyte may be avoided by comparing detection spectrums corresponding to measurement regions of a biological material and sensing a noise signal or an abnormal signal which may occur based on a position of each of the measurement regions. Therefore, only a certain spectrum signal having a high contribution degree corresponding to the target analyte of the biological material may be selected and analyzed, and a Signal to Noise Ratio (SNR) may also be improved. Furthermore, a target measurement value of the target analyte of the biological material may be calculated in real time by measuring the detection spectrums corresponding to the measurement regions provided on mutually different positions of the biological material, and differentiating the detection spectrums.

It should be understood that the exemplary embodiments described herein should be considered in a descriptive sense only and not for purposes of limitation. Also, descriptions of features and/or aspects within each exemplary embodiment should typically be considered as available for other similar features and/or aspects in other exemplary embodiments.

While exemplary embodiments have been described with reference to the figures, it should be understood by those of ordinary skill in the art that various changes in form and details may be made to the exemplary embodiments without departing from the spirit and scope as defined by the following claims.

What is claimed is:

1. A spectroscopic apparatus for analyzing a biological material having an internal non-uniform tissue depending on a position thereof, the spectroscopic apparatus comprising:
  a detector having a plurality of apertures, each of the plurality of apertures configured to obtain a respective detection spectrum of respective detection spectrums corresponding to a plurality of measurement regions that are disposed at mutually different positions of the biological material and correspond to each of the plurality of apertures, respectively; and
  an information processor configured to differentiate the respective detection spectrums and analyze the biological material based on the differentiating.

2. The spectroscopic apparatus of claim 1, wherein each of the plurality of measurement regions is formed of a multi-layered structure including two or more layers which are stacked, and
  each of the two or more layers is formed of a non-uniform thickness depending on the mutually different positions of the plurality of measurement regions.

3. The spectroscopic apparatus of claim 2, wherein the two or more layers forming each of the plurality of measurement regions differ from one another in contribution degrees of data for the respective detection spectrum of each of the plurality of measurement regions.

4. The spectroscopic apparatus of claim 1, wherein the information processor is further configured to determine whether at least one of the plurality of measurement regions is abnormal by mutually comparing the respective detection spectrums and determining whether at least one of the respective detection spectrums corresponding to the at least one of the plurality of measurement regions includes a noise signal or an abnormal signal.

5. The spectroscopic apparatus of claim 1, wherein the information processor is further configured to convert differential spectrums obtained by differentiating the respective detection spectrums into contribution degrees of data for a target analyte of the biological material.

6. The spectroscopic apparatus of claim 5, wherein the information processor is further configured to calculate a target measurement value for the target analyte of the biological material at an optional time using the contribution degrees of data for the target analyte of the biological material.

7. The spectroscopic apparatus of claim 1, wherein the detector is configured to obtain the respective detection spectrums using a Raman spectroscopy or a near infrared spectroscopy.

8. The spectroscopic apparatus of claim 1, wherein each of the plurality of apertures is further configured to be disposed adjacent to a surface of the biological material and receive a light signal from a measurement region among the plurality of measurement regions.

9. The spectroscopic apparatus of claim 1, wherein the biological material comprises a skin, and
  the information processor is further configured to measure a blood glucose in real time using the respective detection spectrums obtained at the mutually different positions on the skin.

10. The spectroscopic apparatus of claim 1, wherein each of the plurality of apertures is further configured to contact a skin surface of a measurement region among the plurality of measurement regions at the mutually different positions, respectively.

11. The spectroscopic apparatus of claim 1, wherein the detector is one of a plurality of detectors, each of the plurality of detectors having each of the plurality of apertures, respectively, and the plurality of detectors is configured to simultaneously obtain the respective detection spectrums, respectively.

12. A spectroscopic method for analyzing a biological material having an internal non-uniform tissue depending on a position thereof, the spectroscopic method comprising:

obtaining, by each of a plurality of apertures of a detector, a respective detection spectrum of respective detection spectrums corresponding to a plurality of measurement regions that are disposed at mutually different positions of the biological material and correspond to each of the plurality of apertures, respectively; and determining whether at least one measurement region of the plurality of measurement regions is abnormal by mutually comparing the respective detection spectrums and determining whether at least one of the respective detection spectrums corresponding to the at least one measurement region includes a noise signal or an abnormal signal.

13. The spectroscopic method of claim 12, wherein each of the plurality of measurement regions is formed of a multi-layered structure including two or more layers which are stacked, and each of the two or more layers is formed of a non-uniform thickness depending on the mutually different positions of the plurality of measurement regions.

14. The spectroscopic method of claim 12, further comprising changing a position of the at least one measurement region determined to be abnormal based on the determining that the at least one measurement region includes the noise signal or the abnormal signal.

15. A spectroscopic method for analyzing a biological material having an internal non-uniform tissue depending on a position thereof, the spectroscopic method comprising:

obtaining, by each of a plurality of apertures of a detector, a respective detection spectrum of respective detection spectrums corresponding to a plurality of measurement regions that are disposed at mutually different positions of the biological material and correspond to each of the plurality of apertures, respectively;

differentiating the respective detection spectrums;

converting the differentiated detection spectrums into contribution degrees of data for a target analyte of the biological material; and analyzing the biological material using the contribution degrees of data.

16. The spectroscopic method of claim 15, wherein each of the plurality of measurement regions is formed of a multi-layered structure including two or more layers which are stacked, and each of the two or more layers is formed of a non-uniform thickness depending on the mutually different positions of the plurality of measurement regions.

17. The spectroscopic method of claim 16, wherein the two or more layers forming each of the plurality of measurement regions differ from one another in the contribution degrees of data for the respective detection spectrum of each of the plurality of measurement regions.

18. The spectroscopic method of claim 15, further comprising calculating a target measurement value for the target analyte of the biological material at an optional time using the contribution degrees of data for the target analyte of the biological material.

19. The spectroscopic method of claim 18, wherein the calculating the target measurement value for the target analyte comprises:

measuring actual values for the target analyte of the biological material at a first point in time;

converting differential spectrums obtained by differentiating the respective detection spectrums acquired at the first point in time into first contribution degrees of data for the target analyte of the biological material;

correlating the first contribution degrees of data to the actual values measured at the first point in time;

converting differential spectrums obtained by differentiating the respective detection spectrums acquired at a second point in time into second contribution degrees of data for the target analyte of the biological material; and calculating the target measurement value for the target analyte of the biological material at the second point in time by comparing the second contribution degrees of data with the first contribution degrees of data.

20. The spectroscopic method of claim 15, wherein the biological material comprises a skin, and the spectroscopic method further comprises measuring blood glucose in real time using the respective detection spectrums obtained at the mutually different positions on the skin.

21. A spectroscopic apparatus for detecting a biological material, the spectroscopic apparatus comprising:

a detector having a plurality of apertures, each of the plurality of apertures configured to obtain a respective detection spectrum among a plurality of detection spectrums from a plurality of measurement regions that are disposed at mutually different positions of the biological material and correspond to each of the plurality of apertures, respectively; and an information processor configured to compare the plurality of detection spectrums with each other, detect at least one detection spectrum that includes noise, and calculate a target measurement value for an analyte of the biological material using detection spectrums among the plurality of detection spectrums that do not include the noise.

22. The spectroscopic apparatus of claim 21, wherein the detector is one of a plurality of detectors, and each of the plurality of detectors is configured to obtain the respective detection spectrum from a respective position among the mutually different positions on the biological material.

23. The spectroscopic apparatus of claim 21, wherein each of the plurality of measurement regions comprises a three-dimensional (3D) region formed from a surface of the biological material to a depth thereof.

* * * * *